(12) United States Patent
Moore-Ede

(10) Patent No.: US 9,241,658 B2
(45) Date of Patent: Jan. 26, 2016

(54) PERSONAL FATIGUE RISK MANAGEMENT SYSTEM AND METHOD

(71) Applicant: Martin Christopher Moore-Ede, Wellesley, MA (US)

(72) Inventor: Martin Christopher Moore-Ede, Wellesley, MA (US)

(*) Notice: Subject to any disclaimer, the term of this patent is extended or adjusted under 35 U.S.C. 154(b) by 343 days.

(21) Appl. No.: 13/622,720

(22) Filed: Sep. 19, 2012

(65) Prior Publication Data

US 2014/0081179 A1     Mar. 20, 2014

(51) Int. Cl.
*A61B 5/103* (2006.01)
*A61B 5/11* (2006.01)
*A61B 5/18* (2006.01)
*A61B 5/00* (2006.01)

(52) U.S. Cl.
CPC ............... *A61B 5/1118* (2013.01); *A61B 5/18* (2013.01); *A61B 5/681* (2013.01); *A61B 5/7275* (2013.01); *A61B 2562/0219* (2013.01)

(58) Field of Classification Search
CPC ..... A61B 5/4528; A61B 5/1071; A61B 5/103
USPC ............................ 600/587, 595; 20/587, 595
See application file for complete search history.

(56) References Cited

U.S. PATENT DOCUMENTS

| | | | | |
|---|---|---|---|---|
| 5,682,882 | A * | 11/1997 | Lieberman | 600/301 |
| 8,647,287 | B2 * | 2/2014 | Greenberg et al. | 600/595 |
| 2004/0049132 | A1 * | 3/2004 | Barron et al. | 600/595 |
| 2006/0200008 | A1 * | 9/2006 | Moore-Ede | 600/300 |
| 2007/0208542 | A1 * | 9/2007 | Vock et al. | 702/187 |
| 2010/0100004 | A1 * | 4/2010 | van Someren | 600/549 |
| 2012/0078063 | A1 * | 3/2012 | Moore-Ede | 600/300 |
| 2012/0316455 | A1 * | 12/2012 | Rahman et al. | 600/547 |
| 2013/0018284 | A1 * | 1/2013 | Kahn et al. | 600/595 |

* cited by examiner

*Primary Examiner* — Sean Dougherty
*Assistant Examiner* — Daniel Cerioni
(74) *Attorney, Agent, or Firm* — Norton Rose Fulbright US LLP

(57) ABSTRACT

A system and method for personal fatigue risk management, performed using a smartwatch including a digital processor, associated memory, and an accelerometer for measuring acceleration in X, Y, and Z axes. A signal is received from the accelerometer indicating a movement of the smartwatch, and the value of the signal is stored in association with indicia of the time at which the signal was received in a time-stamped bin. The stored movement values are analyzed using a state algorithm to determine sleep, wake, and off-wrist state values. Fatigue risk values are determined from the sleep and wake state values, using a state algorithm. The probable relative risk of errors and incidents as compared to average risk, for the wearer of the watch, are then calculated. A warning is issued when the fatigue risk data indicates that one of the thresholds has been exceeded.

18 Claims, 8 Drawing Sheets

PERSONAL FATIGUE RISK MANAGEMENT SYSTEM AND METHOD

BACKGROUND PROBLEM TO BE SOLVED

Fatigue risk management is critical to employee safety, health and productivity in continuous operations where people work extended hours on rotating or night shifts. However, employees (and their managers) often lose track of how much sleep debt they are accumulating and how fatigue-impaired they are, and they often do not know what they should do to mitigate this risk. Without this vital information, fatigue may become uncontrolled, increasing the rate of errors, accidents and injuries, and impairing employee productivity and effective decision-making.

SOLUTION/SUMMARY

A portable smartwatch-based device is disclosed for providing a personal Fatigue Risk Management System (FRMS), measuring sleep and/or activity data, predicting fatigue risk and providing advice to help an individual mitigate their fatigue risk, either using only the smartwatch, or by communicating with and using other portable computer processing devices, such as smart phones, as part of the personal FRMS.

The present system and method for personal fatigue risk management is performed using a smartwatch which includes a digital processor, associated memory, and an accelerometer for measuring acceleration in multiple axes. In operation, a signal is received from the accelerometer indicating a movement of the smartwatch, and the value of the signal is stored in association with indicia of the time at which the signal was received in a time-stamped bin. The stored movement values are analyzed using a state algorithm to determine sleep, wake, and off-wrist state values. Fatigue risk values are determined from the sleep and wake state values, using a state algorithm. The probable relative risk of errors and incidents as compared to average risk, for the wearer of the watch, are then calculated. A warning is issued when the fatigue risk data indicates that one of the thresholds has been exceeded.

DETAILED DESCRIPTION

The present system and method employs a smartwatch programmed to assess fatigue, provide fatigue-related advice and warnings, and improve safety results over existing prescriptive safety regulations. As used herein, the term "smartwatch" refers to a device, wearable on a person's wrist, that includes a digital processor and memory available for computing tasks in addition to those related only to timekeeping.

Figure 1A:
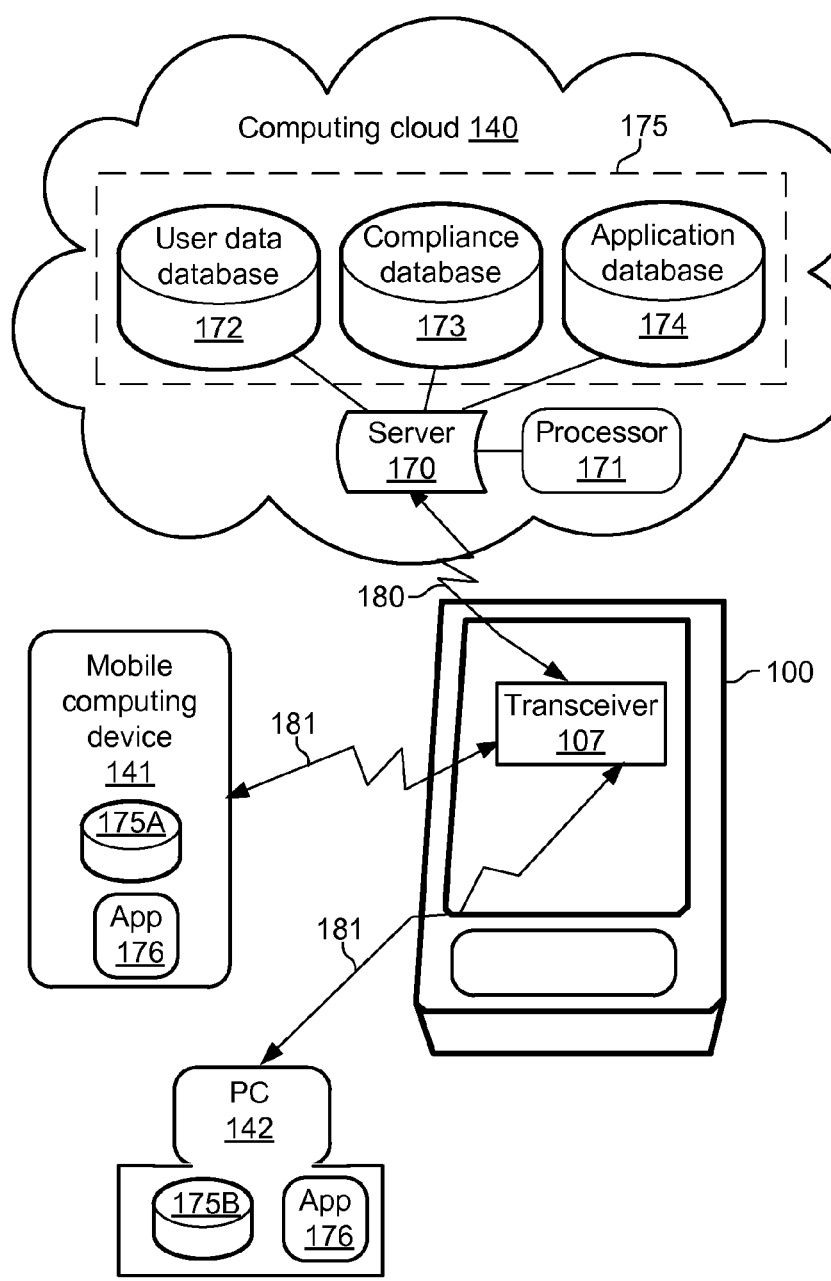
FIG. 1A is a system diagram showing an exemplary computing environment in which the present system and method operates.

FIG. 1A is a system diagram showing an exemplary computing environment in which the present FRMS (Fatigue Risk Management System) smartwatch device 100 and associated method operate. As shown in FIG. 1C, smartwatch device 100 may wirelessly communicate, via transceiver 107, with external/remote devices including a PC (personal computer) 142, a mobile computing device 141 such as a smartphone or tablet PC, and/or other computing and data storage devices, via cloud 140. In an exemplary embodiment, computing cloud 140 includes a server 170 which provides communication between device 100 and databases including user data database 172, compliance and standards database 173, and application database 174, which collectively form combined database 175. Server 170 is also communicatively coupled with at least one processor 171 which may execute system algorithms and other system software application programs stored in application database 174, including algorithms and applications 151-156.

In exemplary embodiments, communication between smartwatch device 100 and either mobile computing device 141 or PC 142 is via a wireless protocol 181 such as Bluetooth, and between device 100 and computing cloud 140 is via a wireless local area network protocol 180 such as Wi-Fi. Devices 141 and 142 may contain local copies 175A and 175B, respectively, of combined database 175, or optionally, may communicate with a remote database, such as database 175 to download data as needed.

A smartwatch control application program 150 resides in devices 141 and 142 to enable communication with, downloading of, or execution of applications (e.g., fatigue risk algorithm 154) required to support functions not performed by smartwatch device 100 in certain embodiments.

Figure 1B:
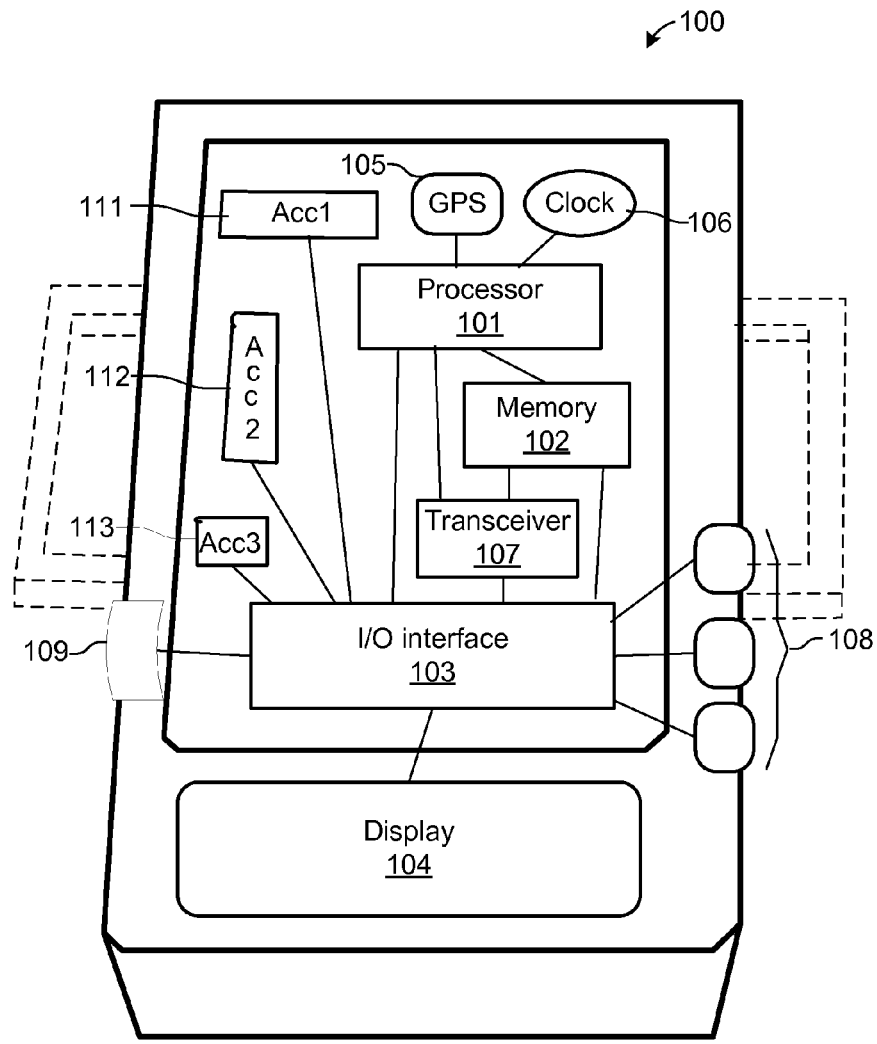
FIG. 1B is a diagram showing exemplary components of a smartwatch-based device configured in accordance with the present system.
Figure 1C:
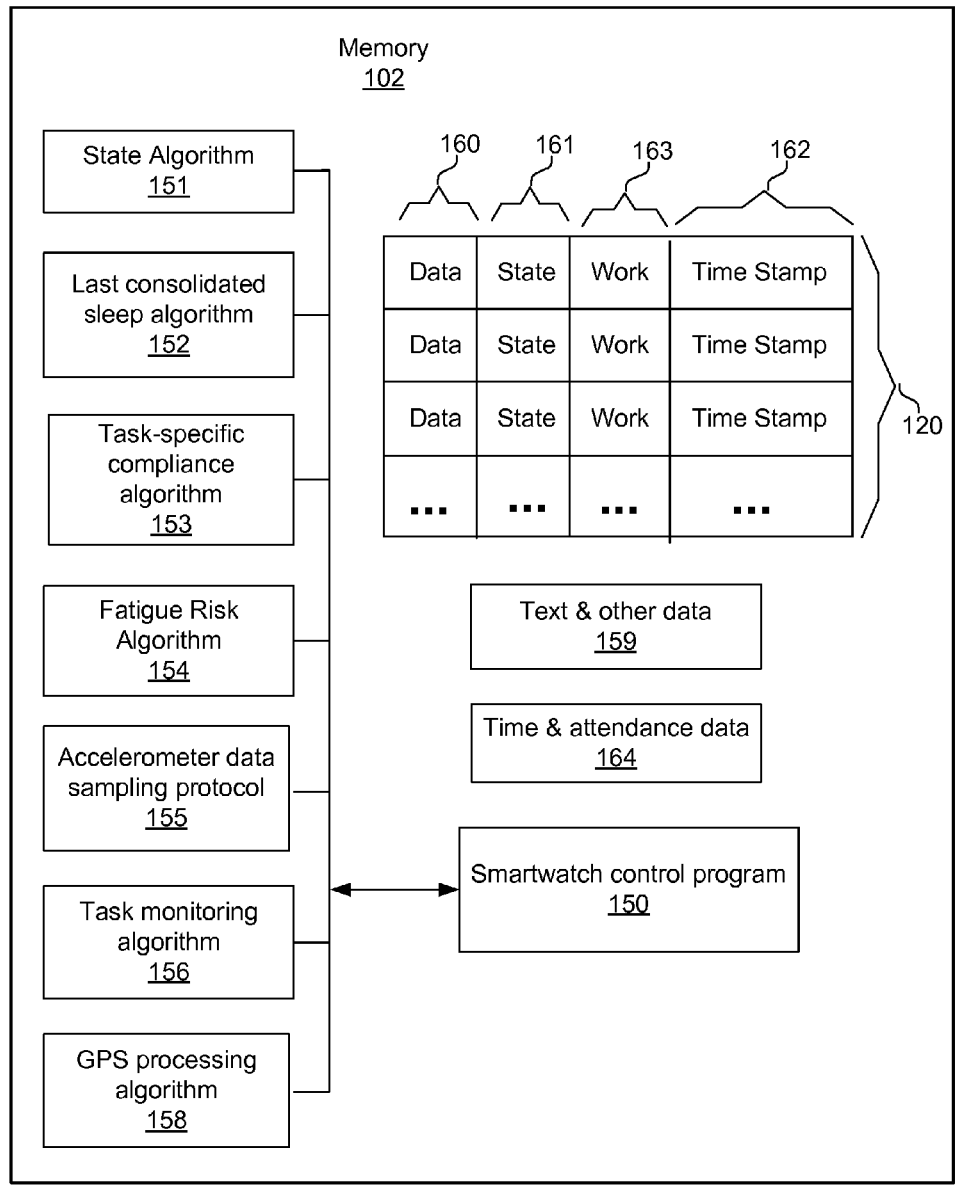
FIG. 1C is an exemplary diagram showing system memory including data, software algorithms and other software used for implementation of the present method.

FIG. 1B is a diagram showing exemplary components of a smartwatch-based FRMS device 100 for personal fatigue risk management in accordance with the presently described system and method. The hardware platform for device 100 may be a pre-existing smartwatch platform such as smartwatches manufactured by Meta Watch or Pebble Technology. Multiple software applications can be executed on smartwatches such as these, which include a 3-axis accelerometer. These smartwatch devices may connect via a wireless protocol, such as Bluetooth®, to a smartphone or tablet PC, such as an iPhone® or Android® device. Alternatively, device 100 may be implemented as a dedicated smartwatch device.

As shown in FIG. 1A, in addition to a clock 106 and display 104, FRMS smartwatch device 100 includes a processor 101 and associated memory 102, an I/O interface 103 for communication with external devices (via transceiver 107 or jack 109), and for receiving user input via a plurality of buttons 108, which may optionally be part of a touch-pad (not shown) on the device. In an exemplary embodiment, smartwatch device 100 also includes three XYZ (mutually orthogonally situated) accelerometers 111, 112, 113 or an equivalent accelerometer that measures acceleration in the X, Y, and Z axes, used to determine the wearer's wrist activity. Device 100 may optionally include a GPS (Global Positioning System) receiver or other location-determining device 105.

FIG. 1C is an exemplary diagram showing system memory 102, which stores information including time-stamped data 120, text (e.g., for advice and other system messages) and other data 159, software algorithms 151-155, and control software 150 used for implementation of the presently described method. Software 150 and algorithms 151-155 for controlling device 100 may optionally be installed in device 100 as firmware.

Actigraphy and other event data is stored in time-stamped bins 120, each comprising a segment of memory locations in system memory 102. In an exemplary embodiment, each time-stamped bin ('time bin') 120 includes accelerometer data 160, an indicator 161 of the user/watch state (e.g., sleep, wake, or off-wrist), an indicator of whether the watch user is on-duty (D) or off-duty (O), and a corresponding time stamp 162 indicating the day and time of acquisition of the data. In an exemplary embodiment, each time bin 120 contains data for a 2 minute interval, although the duration of the interval may be greater or smaller than 2 minutes. System accuracy improves, with diminishing returns, as the bin time interval is decreased, and bin intervals significantly greater than 2 minutes may provide correspondingly less accurate predictive results.

Figure 2A:
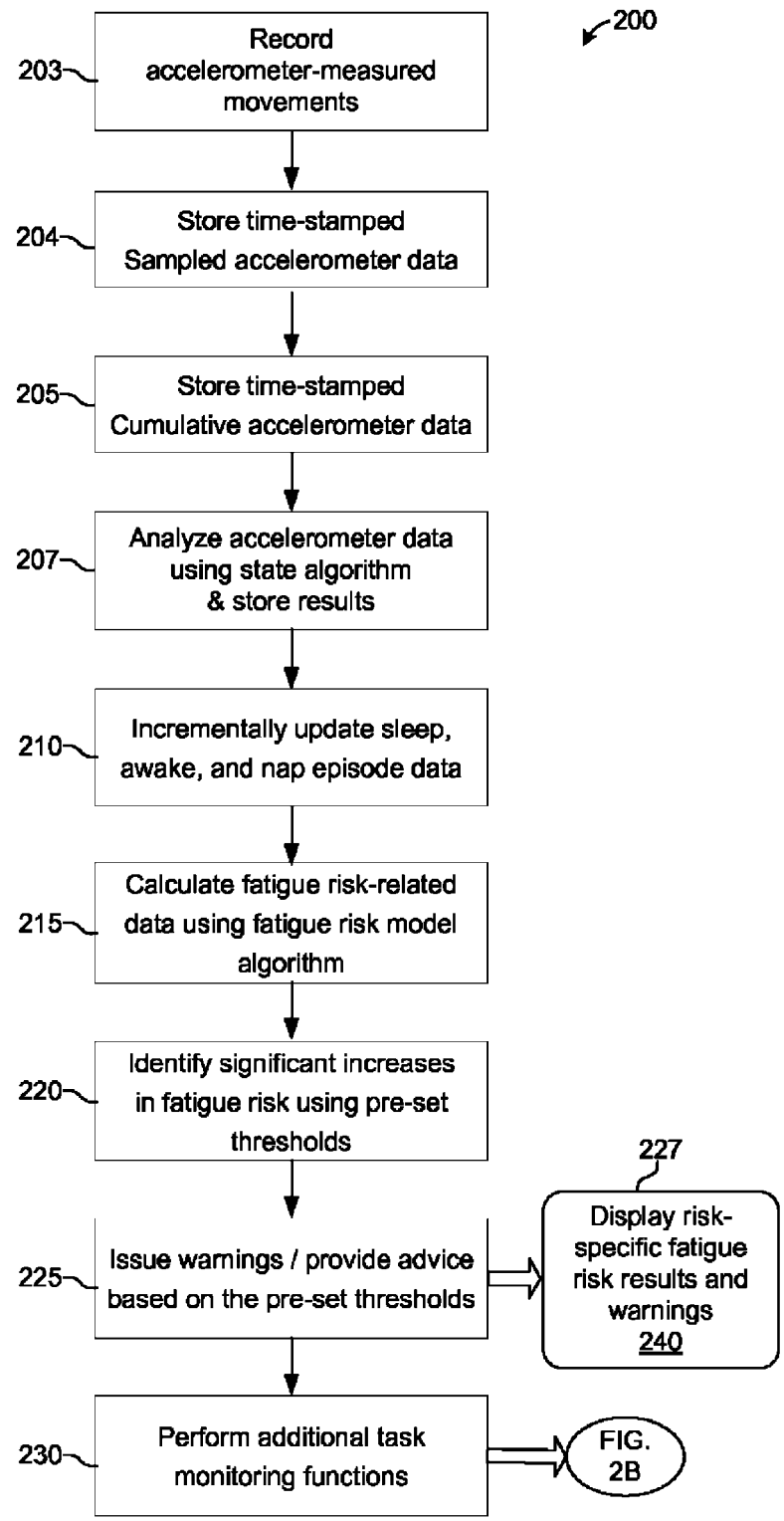
FIGS. 2A and 2B are flowcharts of high-level exemplary algorithms for the present method for personal fatigue risk management.
Figure 2B:
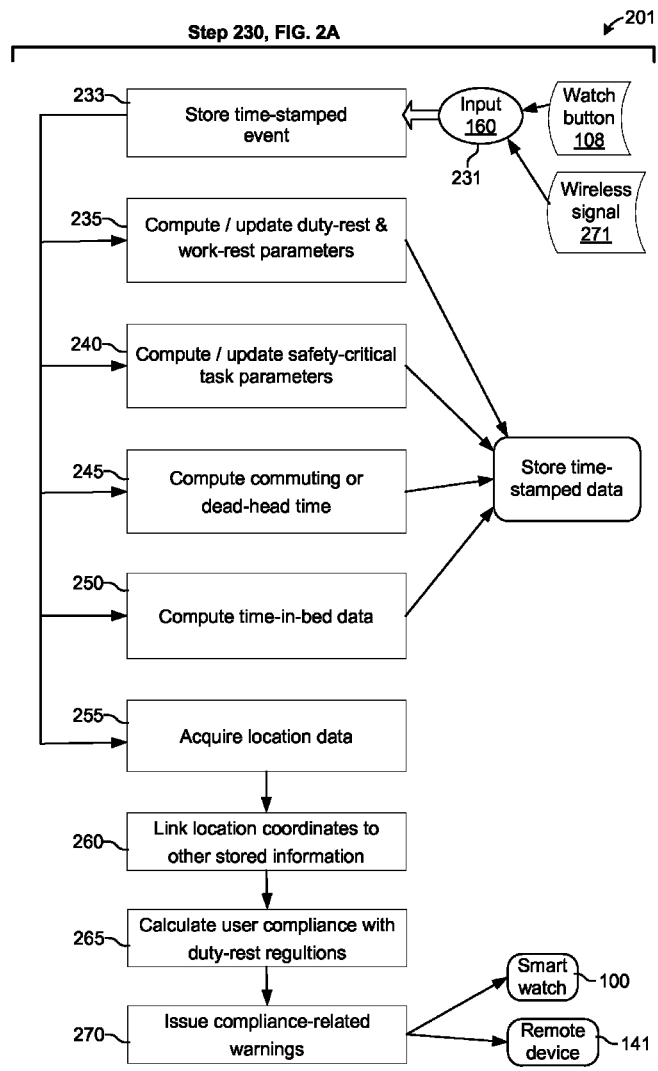
Figure 3:
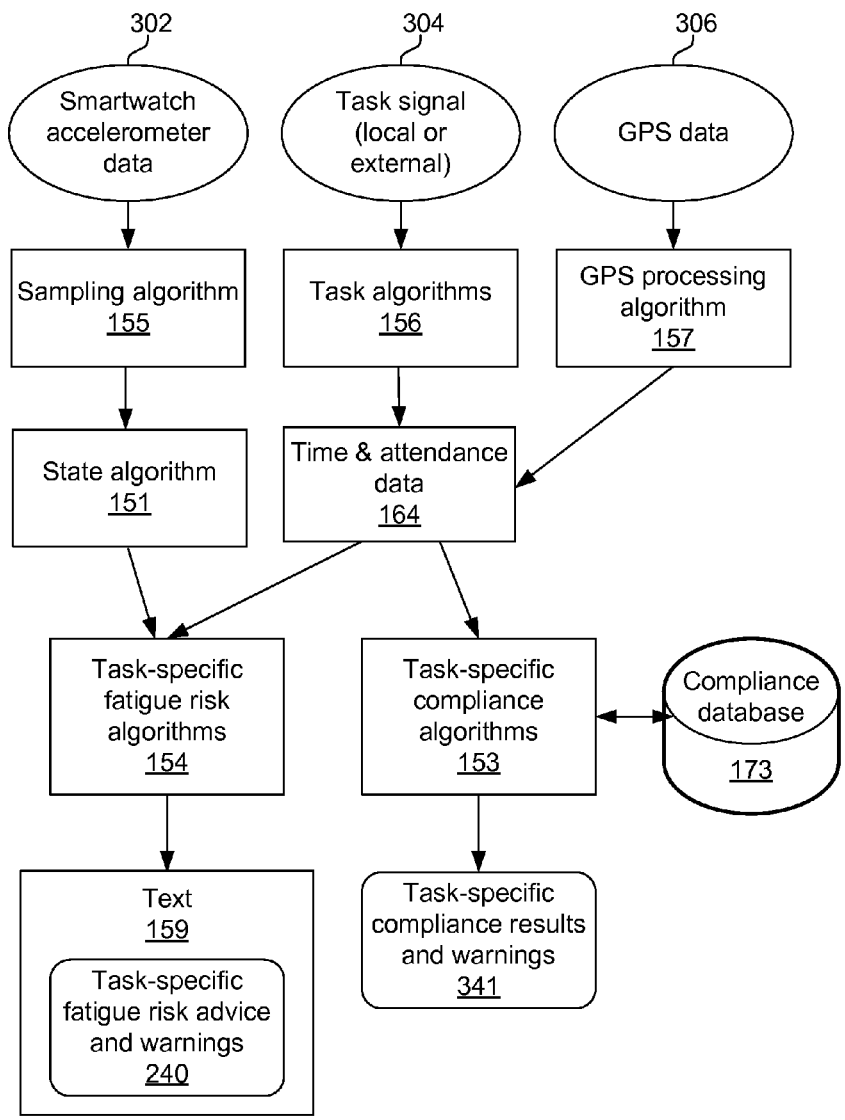
FIG. 3 is an exemplary diagram showing relationships between system data (input data and stored data), processing algorithms, and system-generated results.

FIGS. 2A and 2B are flowcharts showing high-level exemplary algorithms of the present method for personal fatigue risk management. FIG. 3 is an exemplary diagram showing relationships between system data (input data and stored data), processing algorithms, and system-generated results. Operation of the present system is best understood by referring to FIGS. 1A-C, 2A-B, and 3 in conjunction with one another.

As shown in FIG. 2A, at step 203, accelerometer-measured movements of a person's wrist or other body part (e.g., ankle) are recorded. In an exemplary embodiment, as indicated in FIG. 3, data input 302 from accelerometers 111/112/113 is sampled, using sampling algorithm 155. Sampling is performed continuously, 24 hours a day for multiple consecutive days by sampling the accelerometer X, Y and Z coordinate data at intervals, e.g., every 10 seconds, and computing the body part movement. The sampled accelerometer data is then stored in a time-stamped bin, at step 204. At step 205, the accelerometer movement data is stored as average values per one-minute, or two-minute or other short length intervals in a time-stamped bin 120.

Figure 4:
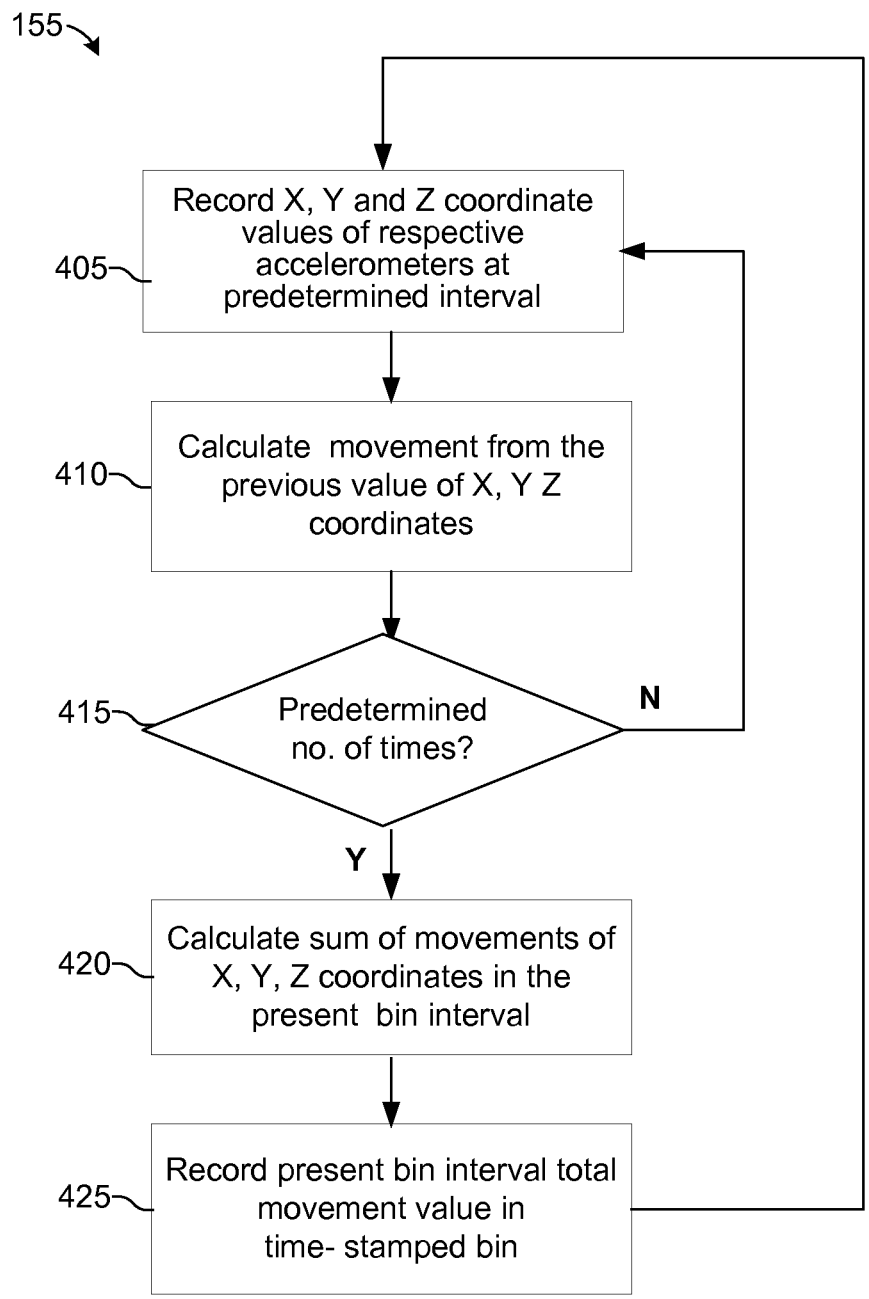
FIG. 4 is a flowchart indicating the protocol used for sampling accelerometer data.

FIG. 4 is a flowchart of an exemplary algorithm 155 indicating the protocol used for sampling accelerometer data. As shown in FIG. 4, at step 405, X, Y and Z coordinate values of respective accelerometers 111, 112, and 113 are recorded at every predetermined interval, such as every 10 seconds, in device memory 120. Alternatively, the accelerometer measures only values determined from two of the X, Y or Z coordinates. At step 410, the movement (displacement, or change in position in space) from the previous value of X, Y Z coordinates is calculated. This process is then repeated (step 415) a predetermined number of times (e.g., 12 times) over an interval equal to the present bin interval (e.g., 2 minutes). The cumulative sum of movements in X, Y, Z coordinates in the (e.g., 2 minute) bin interval is then calculated, at step 420. Next, at step 425, the present bin interval (2 minute) total movement value is recorded in a time-stamped bin 120 (the prior X, Y, Z coordinate values can be overwritten). The above process is then repeated on a continuous basis.

As shown in FIG. 2A, at step 207, the accelerometer data 302 is analyzed using state algorithm 151 (described below), by look-back weighted averaging of time-stamped bins 120 to determine the "sleep", "wake", or "off-wrist" state values (S, W, O, respectively) of the user, incrementally in each time bin 120. Looking back at the most recent time bin and a predetermined number of previous time bins (e.g., 10), an S, W or O transition, if any, is identified. A state indicator 161 indicating the calculated S, W, or O value is then stored in time stamped bins 120, using the time and date from time clock 108 in device 100.

A sleep scoring algorithm 151 (hereinafter referred to as state algorithm 151) is used to enable a computing device to make sleep vs. wake distinctions from wrist movement accelerometer data, to allow determination of the lengths of time a subject user is asleep or awake. One widely-known method of scoring actigraphy data is an algorithm developed by Cole and Associates, and described in their article entitled "Automatic Sleep/Wake Identification from wrist Actigraphy", pub. in *Sleep*, vol. 15, pp. 461-469 (1992). The present method uses state algorithm 151 to determine a user's sleep and wake states, as well as 'off-wrist' states for device 100.

Figure 5:
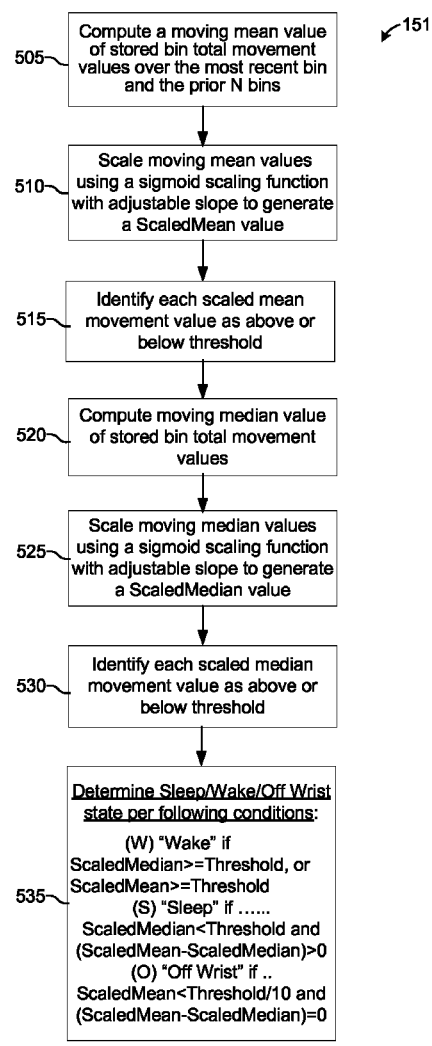
FIG. 5 is a flowchart of an exemplary algorithm for determining sleep-wake state transitions.

FIG. 5 is a flowchart of an exemplary state algorithm 151 for determining sleep-wake state transitions. As shown in FIG. 5, at step 505, a moving mean value of stored (e.g., in 2-minute bins 120) total movement values over the most recent bin and the prior N (e.g., a predetermined number such as 10) bins is computed. At step 510, the moving mean values are scaled to generate a scaled mean movement value ("ScaledMean") using a sigmoid scaling function with adjustable slope.

Next, using a threshold value (e.g., 0.2 on scaled mean scale), each scaled mean movement value is identified as either above threshold or below threshold, at step 515, and a moving median value of stored bin total movement values over the most recent bin and the prior 10 bins is computed, at step 520.

The moving median values are then scaled using a sigmoid scaling function with adjustable slope to generate a scaled median value ("ScaledMedian"), at step 525. Next, using a threshold value (e.g., 0.2 on scaled median scale), each scaled median movement value is identified as either above threshold or below threshold ("Threshold"), at step 530.

In step 535, the following conditions are utilized to determine Sleep/Wake/Off Wrist state:
- (W) "Wake" if ScaledMedian>=Threshold, or ScaledMean>=Threshold
- (S) "Sleep" if ScaledMedian<Threshold and (ScaledMean-ScaledMedian)>0
- (O) "Off Wrist" if ScaledMean<Threshold/10 and (ScaledMean-ScaledMedian)=0

Table 1, below, shows an example of data stored in time-stamped 2-minute bins 120 in device memory 102.

TABLE 1

EXAMPLE DATA STORED IN TIME-STAMPED 2-MINUTE BINS

Example Sleep Onset

Time Date

|  | 22560607 | 22580607 | 23000607 | 23020607 | 23040607 | 23060607 | 23080607 | 23100607 | 23120607 | 23140607 |
|---|---|---|---|---|---|---|---|---|---|---|
| Avg Accel | 89 | 56 | 12 | 3 | 0 | 0 | 5 | 1 | 0 | 0 |
| State | W | W | W | S | S | S | S | S | S | S |

TABLE 1-continued

EXAMPLE DATA STORED IN TIME-STAMPED 2-MINUTE BINS

Example Wake Onset

Time Date

| | 06580707 | 07000707 | 07020707 | 07040707 | 07060707 | 07080707 | 07100707 | 07120707 | 07140707 | 07160707 |
|---|---|---|---|---|---|---|---|---|---|---|
| Avg Accel | 0 | 3 | 56 | 42 | 45 | 89 | 5 | 0 | 0 | 0 |
| State | S | S | W | W | W | W | W | O | O | O |

In the example shown in Table 1, a user falls asleep at 11:02 pm on July 6th (which date/time is coded, for example, as "23020706"), and wakes up at 7:02 am on July 7th after sleeping for 8 hours. The user then takes the smartwatch 100 off his wrist and lays it on the counter at 7:12 am on July 7. In the left-hand column of Table 1, "Time" and "Date" collectively correspond to time stamp 162, and "Avg Accel" (average acceleration) corresponds to (and comprises at least part of) data 160, as indicated in FIG. 1C.

Note that the parameter values for the number of bins 120 in the moving window, the slope of the scaling functions, and the threshold values are each adjustable so that they can be optimized to the particular response of the specific accelerometer that is being used in device 100.

At step 210, smartwatch device 100 computes, updates incrementally, and stores sleep-related information each minute (or other frequent time bin interval) looking back (using weighted averaging) in the stored S, W or O state values in the time bins 120. This sleep-related information is generated by a 'last consolidated sleep' algorithm 152, which tabulates the following values:

(a) Time of day of last consolidated sleep episode (i.e., sleep episode longer than 3 hours or other predetermined value) computed from the number of consecutive time bins from the time of beginning sleep (W to S transition), to the time of ending sleep (S to W transition) of each episode of consolidated sleep;

(b) Duration of last consolidated sleep episode, computed from the time interval (i.e. number of consecutive time bins) between the beginning of sleep (W to S transition), and ending of sleep (S to W transition) of each episode of consolidated sleep;

(c) Quality of last consolidated sleep episode (determined from analysis of accelerometer movements during the last consolidated sleep episode);

(d) Time of day of current or most recent time awake episode since the last consolidated sleep episode (beginning with the last S to W transition from consolidated sleep, and ending with the transition from the W to S state;

(e) Duration of current or most recent time awake episode since the last consolidated sleep episode (calculated form the time interval (i.e., number of consecutive time bins) since the last S to W transition from consolidated sleep) and ending with the current time bin, or the transition from W to S state;

(f) Time of day of nap episodes (blocks of time bins in sleep state of less than 3 hours in duration, or other pre-determined value);

(g) Duration of any nap episodes in the time awake episode since the last consolidated sleep episode (computed from the beginning (W to S transition), and end (S to W transition) of each nap episode); and (h) Quality of naps in the time awake since the last consolidated sleep episode (determined from analysis of accelerometer movements during the naps).

At step 215, using the sleep, awake and nap episode values determined in step 210, a fatigue risk algorithm 154 is used to calculate fatigue risk-related data including the probable risk of fatigue impairment, the principal contributors to the fatigue risk, and other measures such as average alertness, time in low alertness, etc., over a predetermined time interval.

CAS Fatigue Risk Model Algorithm

The fatigue risk algorithm 154 used with the present system/method can be of the type described in, for example, U.S. Pat. No. 5,433,223, entitled "Method for Predicting Alertness and Bio-Compatibility of Work Schedule of an Individual," and incorporated herein by reference. Alternatively, the risk model can be a proprietary risk model that is privately developed for exclusive personal use, or may be a risk model that is in the public domain or a risk model used in research in academic institutions.

The fatigue risk model used as the basis for algorithm 154 can be implemented as a commercially available expert system, for example, the Circadian Alertness Simulator (CAS). The CAS includes a software-based expert system that provides a set of flexible sleep management rules for safe operation of trucking fleets. See Moore-Ede M. C., Heitmann A., Guttkuhn R., Trutschel U., Aguirre A., Croke D., "Circadian alertness simulator for fatigue risk assessment in transportation: application to reduce frequency and severity of truck accidents," Aviation, Space, and Environmental Medicine" 2004; 75(3): Suppl A107-18, incorporated herein by reference. CAS simulates alertness and chronic sleep deprivation levels based on actual work patterns. CAS includes simulation modules for sleep and alertness prediction and a cumulative fatigue risk score assessment is calculated across multiple days or weeks.

The CAS model is based on a two-process model of sleep regulation where sleep timing and duration is determined by circadian and a homeostatic components, and on the well-established relationships between the circadian factors (phase, period, amplitude), homeostatic factors (sleep and wake duration) and alertness. See Borbely, A A. "A two process model on sleep regulation," Hum Neurobiol 1982; 1:195-204, incorporated herein by reference. See also Daan S, Beersma D G M, Borbely A A. "Timing of human sleep: recovery process gated by a circadian pacemaker." American Journal of Physiology 1984; 246:R161-R183, incorporated herein by reference. See also Carskadon M A, Dement W C. "Daytime sleepiness: Quantification of a behavioral state," Neuroscience & Biobehavioral Reviews 1987; 11:307-317, incorporated herein by reference. The CAS model assumes a superposition of the homeostatic and circadian processes.

In sleep estimation mode, the CAS algorithm 154 (or other suitable fatigue risk determination algorithm) 154 used in the present system/method calculates alertness minute by minute, and indicates a sleep state when alertness reaches a certain lower threshold, provided that sleep is not prohibited at this point in time (e.g., due to work activity). The CAS algorithm then creates a sleep state for all following minutes until alertness reaches an upper threshold, or a time when sleep is prohibited due to the work schedule and other constraints (e.g., required pre-work preparation and commuting time). At this time, the activity simulation switches to the awake state and assumes wakefulness until sleep is indicated again. This way, the model generates a complete sleep-wake pattern around any given work pattern.

Based on sleep and alertness measures and the actual work-rest pattern, a cumulative sleep deprivation "fatigue score" is calculated for each individual. The cumulative fatigue score quantifies overall sleep deprivation risk across a given time period. It is computed as the weighted sum of several output parameters, such as daily sleep duration, percentage time in defined alertness zones during work, duration of episodes with critically low alertness during work, average alertness score, variability of alertness score, hours of duty per week, and number of recovery breaks allowing two consecutive nights of sleep per week. In one embodiment, the fatigue risk score ranges from 0 (no fatigue) to 100 (extreme fatigue). This score may be scaled so that a Monday-Friday 9 AM-5 PM daytime-only work schedule scores a 5, and a extreme schedule of consecutive cycles of 36 hours continuously on-duty and 12 hours rest with 1 day off per week (e.g. as seen in medical interns) scores a 95 on the scale from 0 to 100.

At step 220, safety-significant increases in fatigue risk are identified, using data from predetermined thresholds. An example computation is described below.

Example Computation of Risk Assessment

Using published reference data, a CAS-determined fatigue score is converted into a multiple of average risk of errors/incidents (e.g., accidents) caused by fatigue. Thus, for example, smartwatch device 100 may display risk indications as follows:

Average risk=1× the average risk over 24 hours of having an error, incident or accident that is caused by fatigue;

50% of average risk over 24 hours of having an error, incident or accident that is caused by fatigue at Fatigue Level<2×=no display (i.e., no display if less than 2×);

Twice average risk=2×;

Five times average risk=5×;

Etc.

At step 225, FRMS smartwatch device 100 may issue a warning 240, based on pre-set (predetermined) thresholds of fatigue risk, via smartwatch display screen 104 or other portable device display screen (e.g., smartphone 141 or PC 142) communicating with device 100 via a wireless protocol such as Bluetooth.

Example

At Fatigue Level<2×: No display
At Fatigue Level=2× to 5×: "Increased Fatigue Risk"
At Fatigue Level>5×: "High Fatigue Risk"

Also, at step 225, device 100 may provide advice 240 to the user on corrective actions to minimize fatigue risk (e.g., stop work and get sleep, take nap, will need two consecutive nights of sleep to recover alertness, and minimize fatigue risk, etc.)

Example

At Fatigue Level<2×: No display
At Fatigue Level=2× to 5×: "Need sleep or nap"
At Fatigue Level>5×: "Stop all high risk tasks"

At step 227, some or all the above measurements and recorded derived values, warnings and or corrective actions may be displayed on the smartwatch display 104 or other portable device display screen (e.g., smartphone 141 or PC 142) communicating with smartwatch 100 via wireless such as Bluetooth), to minimize predicted fatigue impairment risk.

Smartwatch device 100 may also upload any part or all of the above data by Bluetooth, Wi-Fi, or other communication protocol, to external computing entities including smartphone/tablet 141, PC 142, and server 170 in computing cloud 140. These computing entities 141, 142, and/or server 170 may perform any of steps 207-225, communicating wirelessly (e.g., via Bluetooth, or directly to internet, e.g., by Wi-Fi) with a software application executed by an external processor 171 in computing cloud 140. Accordingly, algorithms 151-154 and 156 may be executed on any one or a combination of these external computing entities.

Additional Task Monitoring Functions

In specific embodiments, additional task monitoring functions, described below, may be performed in step 230, using task monitoring algorithm 156. FIG. 2B is a flowchart 201 showing high-level exemplary algorithms for monitoring various tasks performed by a user of smartwatch device 100.

As shown in FIG. 2B, at step 231, smartwatch device 100 accepts task signal input, from a user pressing a button 108 on smartwatch device 100, or in response to a wireless signal 271 (e.g., transmitter in workplace time card or other work time entry system, vehicle engine control module (ECM), aircraft cockpit signal, or the like. The occurrence and timing of one or more events is then recorded at step 233 in time stamped bins 120. These events may include Beginning of Duty, End of Duty (signaled by "On Duty" and "Off-Duty" ("D" and "O") button press), Begin Commute, End Commute, Begin Deadhead, End Deadhead, Begin Safety-critical Task (e.g., driving vehicle, flying plane, operating equipment), End Safety-critical Task, Go to Bed, and/or Arise from Bed.

In alternative embodiments, smartwatch device 100 and/or computing entity 141, 142, and/or 170 processes each type of event data as described below in steps 235-270. Each of the task signals 304 below is processed by a respective task monitoring algorithm 156, from which time and attendance data 164 is computed. Some or all of the data values calculated below may be displayed on smartwatch screen 104.

Duty-Rest & Work-Rest Data

At step 235, the following values in each time-bin 120 (or other time interval data storage mechanism) are computed and incrementally updated (e.g., by overwriting the previous value in a respective time bin 120), looking back at the stored S, W and O states in a predetermined number of existing time bins 120:

Time of day of last off-duty episode, computed from the beginning (On-duty to Off-Duty event transition), and the end (Off-Duty to On-Duty event transition), Duration of last off-duty episode (computed from time interval between (e.g., number of consecutive time bins) between the beginning (On-duty to Off-Duty event transition), and end (Off-Duty to On-Duty event transition), and Duration of current On-Duty episode from the time interval (number of consecutive time bins) since the last recorded Off-Duty to On-Duty event transition.

Safety-Critical Task Data

At step 240, safety-critical task data such as flying time, driving time, equipment operating time, and other safety-sensitive task time is computed and incrementally updated for each current time bin 120 looking back at the stored event values in previous time bins. In one embodiment, the following values are calculated:

Time of day of Safety-Critical-Task episode (computed using the beginning (Begin Task signal), and end (End-Task signal), and Duration of current Safety-Critical-Task episode (consecutive time bins since last Begin Task signal (e.g., indicated by pressing button 108 or other transmitted signal)

Commuting or Deadhead Time Data

At step 245, commuting or deadhead time data is computed and incrementally updated for each current time bin 120, looking back at the stored event values in the time bins: In one embodiment, the following values are calculated:

Time of day of Commuting or Deadhead episode (computed from the beginning (Begin Commute or Begin Deadhead event signal), and end (End-Commute or End-Deadhead event signal), and Duration of current Commuting or Deadhead episode (consecutive time bins since last Begin Commute or Begin Deadhead signal (e.g., indicated by pressing button 108).

Time-in-Bed Data

At step 250, time-in-bed data is computed and incrementally updated for each current time bin 120 looking back at the stored event values in the time bins. In one embodiment, the following values are calculated:

Time of 24-hour day of last Time-In-Bed episode, (computed from the beginning (Begin Bedtime signal to End Bedtime signal (where the signals are initiated by pressing button 108), Duration of last Time-In-Bed episode (computed from the time interval between (i.e. number of consecutive time bins) between the beginning (Begin Bedtime signal (e.g., via button 108) and the End Bedtime signal (e.g., via button 100), and Duration of current Time out of Bed episode calculated from the number of consecutive time bins since the last End Bedtime signal (e.g., via button 108).

Optional Additional Location Information

In one embodiment, smartwatch location data 306 is acquired, at step 255, using a GPS (Global Positioning System) function in smartwatch device 100. Location data may, alternatively, be uploaded to device 100 from a workplace time clock or vehicle ECM system or other external location source, by Bluetooth or other electronic communication. Under control of a GPS processing algorithm 157, this linked time and location data is stored in smartwatch memory 102 or offloaded to server database as a record of duty-rest times, time and attendance, and other similar record-keeping data. Location coordinate information 306 is linked to other stored information in the smartwatch device 141 such as Begin Duty, and End Duty events, at step 260.

At step 265, using task-specific compliance algorithm 153 and data stored in compliance database 173, the user's compliance with duty-rest regulations (e.g., Hours of Service, API-RP-755 ANSI standard, flight time/duty time regulations, etc.) is determined and recorded. At step 270, compliance-related warnings 341 may be displayed on smartwatch screen 104 or other portable device (e.g., smartphone 141) indicating lack of compliance, or predicted time until a lack of compliance event will occur (e.g., "you may legally drive for only 30 minutes more").

Combination of Sleep, Wake & Fatigue Data with Task Data and/or Location Data

The sleep, wake and fatigue results, calculated above, may be combined with task timing data, and/or with location data to calculate, store, record and display information such as fatigue risk on duty, fatigue risk while driving, etc. These sleep, wake and fatigue results may be combined with time-in-bed data, and/or with location data, to calculate, store, record and display information such as sleep efficiency (percent time asleep while in bed). In addition, any of the above-described measurements and recorded derived values, warnings and or corrective actions may be displayed on a smartwatch screen 104 to minimize predicted fatigue impairment risk, or to help avoid non-compliance.

All of the above-described functions may be performed in FRMS smartwatch device 100. The only functions that must be conducted in the smartwatch are the accelerometer data collection, the S, W and O state determination and the cumulative displays of hours of sleep and hours awake, so that the smartwatch device provides a real-time record without requiring an interface with another computing platform.

Functions such as the fatigue risk calculation using CAS may be performed on other computing platforms (e.g., smart phone, tablet, PC, etc.) with updates performed via a wireless protocol such as Bluetooth, for example, so that input data to the algorithms may be updated and results may also be displayed on the smartwatch, although these functions may be performed on the smartwatch. More complex functions (e.g., prediction of future risk depending on proposed schedule to be worked, detailed diagnostics, advice on sleep and health issues, etc.) may be computed on other computing platforms, with updates performed via a wireless protocol such as Bluetooth, for example, so that input data to the algorithms may be updated and so that results may be also displayed on the smartwatch.

Having described the invention in detail and by reference to specific embodiments thereof, it will be apparent that modifications and variations are possible without departing from the scope of the invention defined in the appended claims. More specifically, it is contemplated that the present system is not limited to the specifically-disclosed aspects thereof.

What is claimed is:

1. A method for personal fatigue risk management, performed using a smartwatch including a digital processor, associated memory, and an accelerometer for measuring acceleration in X, Y, and Z axes, the method comprising:

a) receiving a signal from the accelerometer indicating an acceleration of the smartwatch and calculating a displacement or change in position of the smartwatch based on this acceleration, the extent of displacement or change in position represented by a movement value;

b) storing the movement value and an indicia of the time at which the signal was received in a time-stamped bin, the time-stamped bin stored in memory locations within the associated memory;

c) repeating steps a) and b) to obtain a plurality of stored movement values for a predetermined time interval;

d) analyzing the plurality of stored movement values, using a state algorithm, to determine a sleep state value, an off-wrist state value or a wake state value for a person wearing the smartwatch for the predetermined time interval;

e) repeating steps a) through d) to obtain a plurality of sleep state values, wake state values, and/or off-wrist state values;

f) receiving a task input or a location input indicative of an activity being performed by a wearer of the smartwatch;

g) analyzing a plurality of the sleep state values and wake state values, using a fatigue risk algorithm, to determine fatigue risk values, the fatigue risk values determined using at least the plurality of sleep state values, wake state values and off-wrist state values, and the task input or the location input indicative of the activity being performed by the wearer of the smartwatch;

h) determining a probable relative risk of errors and incidents indicative of at least a probability of having an error, incident, or accident that is caused at least in part by fatigue as compared to an average risk of errors and incidents for the wearer of the smartwatch, using at least a comparison of the fatigue risk values with a reference index based at least on an aggregate of fatigue-related risk data collected for a plurality of other users and the activity being performed by the wearer of the smartwatch; and i) electronically causing a warning to be issued, via electronic components of the smartwatch, when the probable relative risk of errors and incidents as compared to the average risk of errors and incidents breaches one or more predetermined thresholds for the activity being performed by the wearer of the smartwatch, wherein the warning includes a display indicating one or more corrective actions, the one or more corrective actions selected based on the activity being performed by the wearer of the smartwatch.

2. The method of claim 1, wherein analyzing the plurality of stored movement values to determine the sleep state value, the off-wrist state value and the wake state value further comprises determining a cumulative sum of the stored movement values of the smartwatch during a predetermined time interval and incrementally updating the sleep state value, the off-wrist state value or the wake state value using look-back weighted averaging over the most recent stored movement value and a predetermined number of previous stored movement values.

3. The method of claim 1, further comprising:
recording a time of occurrence of a start or end of activity event selected from the set of events consisting of Beginning of Duty, End of Duty, Begin Commute, End Commute, Begin Deadhead, End Deadhead, Begin Safety-critical Task, End Safety-critical Task, Go to Bed, and Arise from Bed; and
computing and incrementally updating duty-rest parameters and work-rest parameters using look-back weighted averaging of a predetermined number of the stored sleep state values, wake state values, and off-wrist state values;
wherein the duty-rest parameters and work-rest parameters include time of day of last End of Duty event, duration of last off-duty episode, and duration of current on-duty episode since the last recorded Off-Duty to On-Duty event transition.

4. The method of claim 3, wherein the start or end of activity event is wirelessly transmitted by the smartwatch to an external computing device and the incrementally updating is performed by the external device.

5. The method of claim 3, including receiving, from a user pressing a button on the smartwatch, a task signal input indicative of the start of end of activity event(s).

6. The method of claim 3, including receiving, via a wireless signal, the task input; wherein the smartwatch includes a transceiver for communication with a wireless device.

7. The method of claim 3, wherein the smartwatch receives a task input wirelessly from a device selected from the set of devices consisting of a workplace work time entry system, a vehicle engine control module, and an aircraft cockpit signal.

8. The method of claim 1, wherein the smartwatch issues the warning via a display on the smartwatch.

9. The method of claim 1, wherein an indication of the warning is received from a device wirelessly connected to the smartwatch.

10. The method of claim 1, wherein the fatigue risk algorithm is executed on a processing entity, external to the smartwatch, in wireless communication with the smartwatch.

11. The method of claim 1, wherein:
the smartwatch includes a Global Positioning System receiver to acquire location data indicative of the location of the smartwatch; and
the location data is stored in association with corresponding time data and utilized as part of the location input.

12. The method of claim 11, wherein the location data is stored as a record of duty-rest times.

13. The method of claim 11, wherein the location data is stored as a record of time and attendance data.

14. The method of claim 11, further including:
linking the location data to information including Beginning of Duty and End of Duty events;
storing the linked location data;
calculating compliance, of the wearer, with duty-rest regulations, based on the linked location data; and
displaying a warning when a lack of compliance with the regulations is indicated by the calculated compliance.

15. The method of claim 14, wherein a warning is displayed indicating a predicted time until a lack of compliance event will occur.

16. The method of claim 1, further including:
acquiring location data indicative of the location of the smartwatch from one of a Global Positioning System, a workplace time clock, and a vehicle engine control module;
storing the location data in association with corresponding time data;
wherein the location data is stored as a record of one of duty-rest times and time and attendance data;
linking the location data to information including Begin Duty, and End Duty events;
storing the linked location data;
calculating compliance, of the wearer, with duty-rest regulations, based on the linked location data; and
displaying a warning when a lack of compliance with the regulations is indicated by the calculated compliance.

17. The method of claim 16, wherein a warning is displayed indicating a predicted time until a lack of compliance event will occur.

18. The method of claim 1, wherein the accelerometer measures only values determined from two of the X, Y or Z coordinates.

* * * * *